(12) United States Patent
Marion (10) Patent No.: US 10,092,345 B2
(45) Date of Patent: Oct. 9, 2018

(54) SYSTEM AND METHOD OF AN ELECTROSURGICAL CONTROLLER WITH OUTPUT RF ENERGY CONTROL

(71) Applicant: ArthroCare Corporation, Austin, TX (US)

(72) Inventor: Duane W. Marion, Santa Santa, CA (US)

(73) Assignee: ArthroCare Corporation, Austin, TX (US)

( * ) Notice: Subject to any disclaimer, the term of this patent is extended or adjusted under 35 U.S.C. 154(b) by 1420 days.

(21) Appl. No.: 14/032,388

(22) Filed: Sep. 20, 2013

(65) Prior Publication Data
US 2014/0025065 A1 Jan. 23, 2014

Related U.S. Application Data

(62) Division of application No. 12/400,019, filed on Mar. 9, 2009, now Pat. No. 8,574,187.

(51) Int. Cl.
| | |
|---|---|
| *A61B 18/12* | (2006.01) |
| *A61B 18/14* | (2006.01) |
| *A61B 18/18* | (2006.01) |
| *A61B 18/00* | (2006.01) |

(52) U.S. Cl.
CPC ........ *A61B 18/1206* (2013.01); *A61B 18/148* (2013.01); *A61B 18/18* (2013.01); *A61B 2018/00345* (2013.01); *A61B 2018/00404* (2013.01); *A61B 2018/00577* (2013.01); *A61B 2018/00619* (2013.01); *A61B 2018/1472* (2013.01); *A61B 2218/002* (2013.01)

(58) Field of Classification Search
CPC ............................ A61B 18/18; A61B 18/1206
USPC ......................................................... 606/34
See application file for complete search history.

(56) References Cited

U.S. PATENT DOCUMENTS 3,952,748 A * 4/1976 Kaliher .................. A61B 18/12
 219/770
2008/0249523 A1* 10/2008 McPherson ........ A61B 18/1445
 606/41

* cited by examiner

*Primary Examiner* — Alyssa M Alter
(74) *Attorney, Agent, or Firm* — Mark J. Gorman (57) ABSTRACT

An electrosurgical controller with output RF energy control. At least some of the illustrative embodiments are electrosurgical controllers configured to change a first output voltage on the first active terminal relative to the first return terminal by selective control of a number of turns of the primary winding of a transformer used to create the output voltage.

14 Claims, 7 Drawing Sheets

SYSTEM AND METHOD OF AN ELECTROSURGICAL CONTROLLER WITH OUTPUT RF ENERGY CONTROL

CROSS-REFERENCE TO RELATED APPLICATIONS

This application is a divisional of U.S. patent application Ser. No. 12/400,019 filed Mar. 9, 2009, the complete disclosure of which is incorporated herein by reference for all purposes.

BACKGROUND

Electrosurgical systems are used by physicians to perform specific functions during surgical procedures. For example, in an ablation mode electrosurgical systems use high frequency electrical energy to remove soft tissue such as sinus tissue, adipose tissue or other tissue such as meniscus, cartilage, or sinovial tissue in a joint. In a coagulation mode, the electrosurgical device may aid the surgeon in reducing internal bleeding by providing thermal heating and assisting in the coagulation and/or sealing of vessels. In both the ablation and coagulation mode, control of the electrical energy to provide a proper ablation and/or coagulation energy is utilized, and thus any advance that increases the energy control functionality of an electrosurgical system provides competitive advantage.

BRIEF DESCRIPTION OF THE DRAWINGS

For a detailed description of exemplary embodiments, reference will now be made to the accompanying drawings in which.

NOTATION AND NOMENCLATURE

Certain terms are used throughout the following description and claims to refer to particular system components. As one skilled in the art will appreciate, companies that design and manufacture electrosurgical systems may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect electrical connection via other devices and connections.

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this invention belongs.

"Active electrode" shall mean an electrode of an electrosurgical wand which produces an electrically-induced tissue-altering effect when brought into contact with, or close proximity to, a tissue targeted for treatment, and/or an electrode having a voltage induced thereon by a voltage generator.

"Active terminal" shall mean an electrical connection to a transformer that is configured to couple to an active electrode of an electrosurgical wand.

"Return electrode" shall mean an electrode of an electrosurgical wand which serves to provide a current flow path for electrons with respect to an active electrode, and/or an electrode of an electrosurgical wand which does not itself produce an electrically-induced tissue-altering effect on tissue targeted for treatment.

"Return terminal" shall mean an electrical connection to a transformer that is configured to couple to a return electrode of an electrosurgical wand.

"Center tap", in relation to a transformer, shall mean an electrical connection to a winding of the transformer at approximately the middle turn of the total number of turns; however, the center tap need not be precisely at the numeric middle, and a tap that is within 5% of the total number of turns from the numeric middle shall be considered a center tap.

"Fixed", in relation to a direct current (DC) voltage level applied to a winding of a transformer, shall mean a DC voltage level that is either: controlled to a particular DC voltage level during changes in load seen by a secondary of the transformer; or is not adjusted to be a different voltage level in spite of changes in load seen by the secondary of the transformer. The presence of noise (e.g., alternating current (AC) ripple voltages) "riding" the DC voltage level, and drops in voltage caused by current draw of the primary winding, shall not obviate the status of a DC voltage as fixed.

Where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

DETAILED DESCRIPTION

Before the various embodiments are described in detail, it is to be understood that this invention is not limited to particular variations set forth herein as various changes or modifications may be made, and equivalents may be substituted, without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Figure 1:
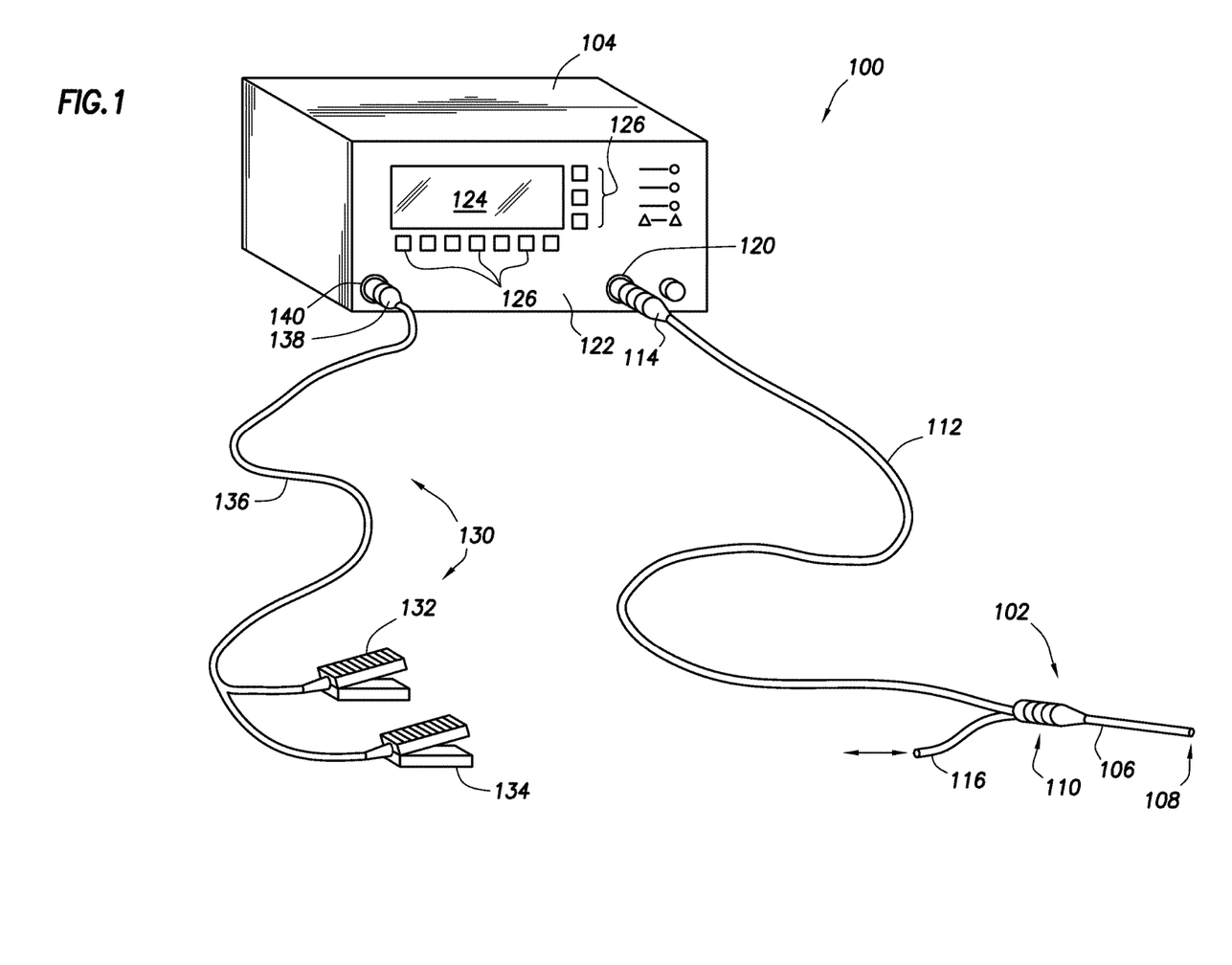
FIG. 1 shows an electrosurgical system in accordance with at least some embodiments.

FIG. 1 illustrates an electrosurgical system 100 in accordance with at least some embodiments. In particular, the electrosurgical system comprises an electrosurgical wand 102 (hereinafter "wand") coupled to an electrosurgical controller 104 (hereinafter "controller"). In some embodiments the wand 102 comprises an elongate shaft 106 that defines distal end 108 where at least some electrodes are disposed. The elongate shaft 106 further defines a handle or proximal end 110, where a physician grips the wand 102 during surgical procedures. The wand 102 further comprises a flexible multi-conductor cable 112 housing a plurality of electrical leads (not specifically shown in FIG. 1), and the flexible multi-conductor cable 112 terminates in a connector 114. Though not visible in FIG. 1, in some embodiments the wand 102 has an internal lumen fluidly coupled to a flexible tubular member 116. The internal lumen and flexible tubular member 116 may be used as a conduit to supply conductive fluid to be proximate to the distal end 108, or the internal lumen and flexible tubular member may be used to aspirate the area proximate to the distal end 108 of the wand 102. Other wand types may be equivalently used.

As shown in FIG. 1, the wand 102 couples to the controller 104, such as by a wand connector 120 on an outer surface 122 (in the illustrative case of FIG. 1 the front surface). A display device or interface panel 124 is visible through the outer surface 122, and in some embodiments a user may select operational modes of the controller 104 by way of the interface device 124 and related buttons 126. In some embodiments the electrosurgical system 100 also comprises an interface device in the form of a foot pedal assembly 130. The foot pedal assembly 130 may comprise one or more pedal devices 132 and 134, a flexible multi-conductor cable 136 and a connector 138. While only two pedal devices 132, 134 are shown, any number of pedal devices may be implemented. The outer surface 122 of the controller 104 may comprise a corresponding pedal connector 140 that couples to the connector 138. A physician may use the foot pedal assembly 130 to control various aspects of the controller 104. For example, a pedal device, such as pedal device 132, may be used for on-off control of the application of radio frequency (RF) energy to the wand 102. As yet another example, a pedal device, such as pedal device 134, may be used to change the RF energy level delivered to the wand 102, such as by a change in the applied voltage.

The electrosurgical system 100 of the various embodiments may have a variety of operational modes. One such mode employs Coblation® technology. In particular, the assignee of the present disclosure is the owner of Coblation® technology. Coblation® technology involves the application of RF energy between one or more active electrodes and one or more return electrodes of the wand 102 to develop high electric field intensities in the vicinity of the target tissue. The electric field intensities may be sufficient to vaporize an electrically conductive fluid over at least a portion of the one or more active electrodes in the region between the one or more active electrodes and the target tissue. The electrically conductive fluid may be inherently present in the body, such as blood, or in some cases extracelluar or intracellular fluid. In other embodiments, the electrically conductive fluid may be a liquid or gas, such as isotonic saline. In some embodiments the electrically conductive fluid is delivered in the vicinity of the active electrodes and/or to the target site by the wand 102, such as by way of the internal passage and flexible tubular member 116.

When the electrically conductive fluid is heated to the point that the atoms of the fluid vaporize faster than the atoms recondense, a gas is formed. When sufficient energy is applied to the gas, the atoms collide with each other causing a release of electrons in the process, and an ionized gas or plasma is formed (the so-called "fourth state of matter"). Stated otherwise, plasmas may be formed by heating a gas and ionizing the gas by driving an electric current through the gas, or by directing electromagnetic waves into the gas. The methods of plasma formation give energy to free electrons in the plasma directly, electron-atom collisions liberate more electrons, and the process cascades until the desired degree of ionization is achieved. A more complete description of plasma can be found in Plasma Physics, by R. J. Goldston and P. H. Rutherford of the Plasma Physics Laboratory of Princeton University (1995), the complete disclosure of which is incorporated herein by reference.

As the density of the plasma becomes sufficiently low (i.e., less than approximately 1020 atoms/cm$^3$ for aqueous solutions), the electron mean free path increases such that subsequently injected electrons cause impact ionization within the plasma. When the ionic particles in the plasma layer have sufficient energy (e.g., 3.5 electron-Volt (eV) to 5 eV), collisions of the ionic particles with molecules that make up the target tissue break molecular bonds of the target tissue, dissociating molecules into free radicals which then combine into gaseous or liquid species. Often, the electrons in the plasma carry the electrical current or absorb the electromagnetic waves and, therefore, are hotter than the ionic particles. Thus, the electrons, which are carried away from the target tissue toward the active or return electrodes, carry most of the plasma's heat, enabling the ionic particles to break apart the target tissue molecules in a substantially non-thermal manner.

By means of the molecular dissociation (as opposed to thermal evaporation or carbonization), the target tissue is volumetrically removed through molecular dissociation of larger organic molecules into smaller molecules and/or atoms, such as hydrogen, oxygen, oxides of carbon, hydrocarbons and nitrogen compounds. The molecular dissociation completely removes the tissue structure, as opposed to dehydrating the tissue material by the removal of liquid within the cells of the tissue and extracellular fluids, as occurs in related art electrosurgical desiccation and vaporization. A more detailed description of the molecular dissociation can be found in commonly assigned U.S. Pat. No. 5,697,882 the complete disclosure of which is incorporated herein by reference.

In addition to the Coblation® mode, the electrosurgical system 100 of FIG. 1 is also useful for sealing larger arterial vessels (e.g., on the order of about 1 millimeter (mm) in diameter), when used in what is known as a coagulation mode. Thus, the system of FIG. 1 has an ablation mode where RF energy at a first voltage is applied to one or more active electrodes sufficient to effect molecular dissociation or disintegration of the tissue, and the system of FIG. 1 has a coagulation mode where RF energy at a second, lower voltage is applied to one or more active electrodes (either the same or different electrode(s) as the ablation mode) sufficient to heat, shrink, seal, fuse, and/or achieve homeostasis of severed vessels within the tissue. In some cases, the ablation mode and coagulation mode are sequentially performed, and in yet still other cases the ablation and coagulation modes are performed simultaneously.

The energy density produced by electrosurgical system 100 at the distal end 108 of the wand 102 may be varied by adjusting a variety of factors, such as: the number of active electrodes; electrode size and spacing; electrode surface area; asperities and/or sharp edges on the electrode surfaces; electrode materials; applied voltage; current limiting of one or more electrodes (e.g., by placing an inductor in series with an electrode); electrical conductivity of the fluid in contact with the electrodes; density of the conductive fluid; and other factors. Accordingly, these factors can be manipulated to control the energy level of the excited electrons. Since different tissue structures have different molecular bonds, the electrosurgical system 100 may be configured to produce energy sufficient to break the molecular bonds of certain tissue but insufficient to break the molecular bonds of other tissue. For example, fatty tissue (e.g., adipose) has double bonds that require an energy level higher than 4 eV to 5 eV (i.e., on the order of about 8 eV) to break. Accordingly, the Coblation® technology in some operational modes does not ablate such fatty tissue; however, the Coblation® technology at the lower energy levels may be used to effectively ablate cells to release the inner fat content in a liquid form. Other modes may have increased energy such that the double bonds can also be broken in a similar fashion as the single bonds (e.g., increasing voltage or changing the electrode configuration to increase the current density at the electrodes). A more complete description of the various phenomena can be found in commonly assigned U.S. Pat. Nos. 6,355,032, 6,149,120 and 6,296,136, the complete disclosures of which are incorporated herein by reference.

While some related art systems may have the ability to perform simultaneous ablation and coagulation, in many cases the simultaneous ablation and coagulation is based on a single RF energy output signal from the controller, with the RF energy signal configured for ablation. The differing applied voltage to stimulate the simultaneous coagulation is created from the single RF energy signal (again, set for ablation) lowered to a coagulation level by a reactive element (i.e., inductor or capacitor) in the electrosurgical wand itself. However, electrosurgical wands are, in most cases, single use disposable devices, and the presence of the reactive element to create the lower coagulation voltage drives up the cost of the electrosurgical wands.

As will be discussed more thoroughly below, the controller 104 in accordance with the various embodiments has separate output signals for ablation and coagulation. Separate output signals enables not only simultaneous ablation and coagulation of tissue, but also eliminates the need for a reactive element within the electrosurgical wand 102. It follows that, in accordance with various embodiments, some if not all the electrodes of wand 102 have individual electrical leads that run from each electrode to the connector 114.

Figure 2:
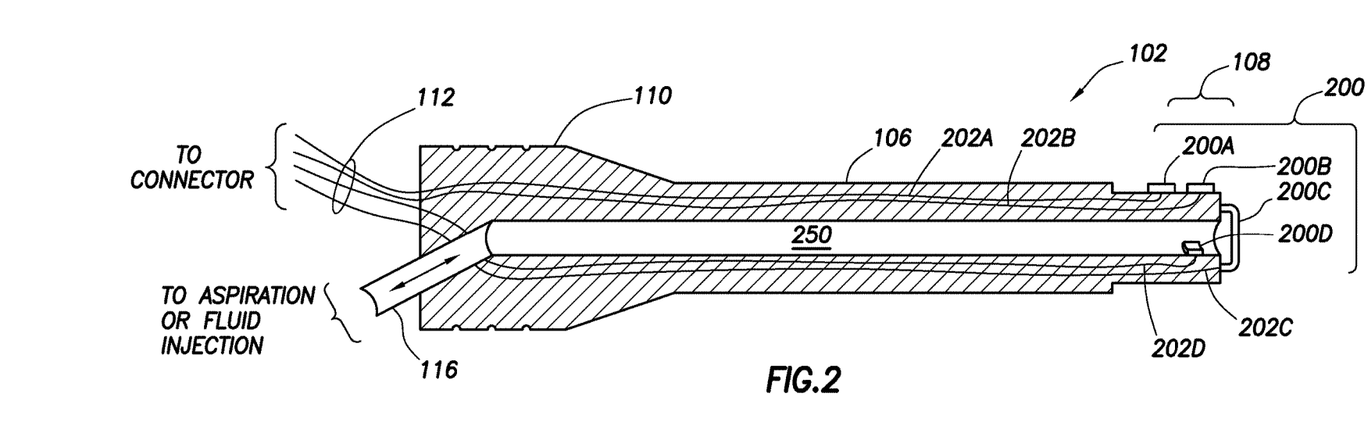
FIG. 2 shows a cross-sectional view of a wand in accordance with at least some embodiments.

FIG. 2 shows a cross-sectional view of wand 102 in accordance with at least some embodiments. In particular, FIG. 2 illustrates the elongate shaft 106 comprising distal end 108 and proximal end 110. Distal end 108 comprises a plurality of electrodes 200. The electrodes of FIG. 2 are merely illustrative, and any arrangement of electrodes may be equivalently used. Each electrode 200 has an electrical lead associated therewith that runs through the elongate shaft 106 to the flexible multi-conductor cable 112. In particular, electrode 200A has dedicated electrical lead 202A which runs within the elongate shaft to the become part of cable 112. Similarly, electrode 200B has dedicated electrical lead 202B which runs within the elongate shaft 106 to become part of cable 112. Illustrative electrodes 200C and 200D likewise have dedicated electrical leads 202C and 202D, respectively, which run within the elongate shaft 106 to become part of cable 112. In some embodiments, the elongate shaft 106 has dedicated internal passages (in addition to optional internal lumen 250) through which the electrical leads 202 run. In other embodiments, the electrical leads 202 are cast within the material that makes up the elongate shaft.

Figure 3:
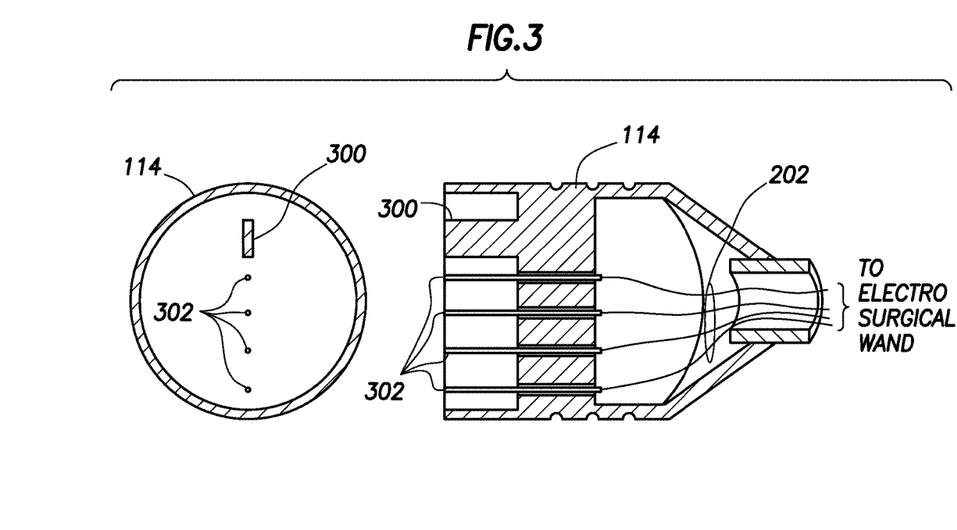
FIG. 3 shows both an elevational end-view (left) and a cross-sectional view (right) of a connector in accordance with at least some embodiments.

As illustrated in FIG. 1, flexible multi-conductor cable 112 (and more particularly its constituent electrical leads 202) couple to the connector 114. Connector 114 couples the controller 104, and more particularly the wand connector 120. FIG. 3 shows both a cross-sectional view (right) and an end elevation view (left) of connector 114 in accordance with at least some embodiments. In particular, connector 114 comprises a tab 300. Tab 300 works in conjunction with a slot on wand connector 120 (shown in FIG. 4) to ensure that the connector 114 and wand connector 120 only couple in one relative orientation. The illustrative connector 114 further comprises a plurality of electrical pins 302 protruding from connector 114. Each electrical pin 302 is coupled to a single electrical lead in the leads 202. Stated otherwise, each electrical pin 302 couples to a single electrical lead 202, and thus each illustrative electrical pin 302 couples to a single electrode 200 (FIG. 2). While FIG. 3 shows only four illustrative electrical pins, in some embodiments 26 or more electrical pins may be present in the connector 114.

Figure 4:
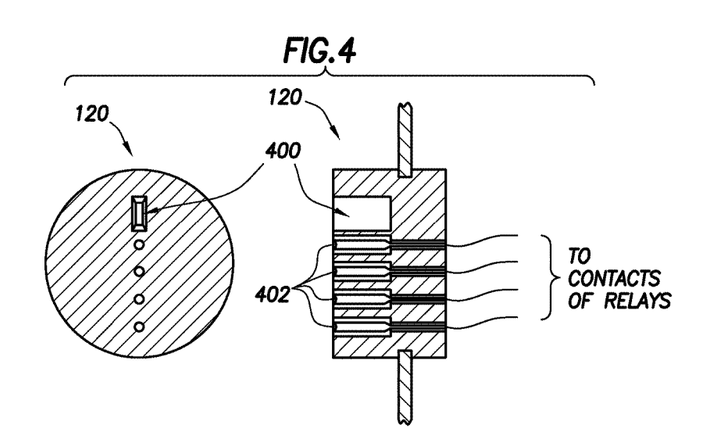
FIG. 4 shows both an elevational end-view (left) and a cross-sectional view (right) of a wand connector in accordance with at least some embodiments.

FIG. 4 shows both a cross-sectional view (right) and an end elevation view (left) of wand connector 120 in accordance with at least some embodiments. In particular, wand connector 120 comprises a slot 400. Slot 400 works in conjunction with a tab 300 on connector 114 (shown in FIG. 3) to ensure that the connector 114 and wand connector 120 only couple in one orientation. The illustrative wand connector 120 further comprises a plurality of electrical pins 402 residing within respective holes of wand connector 120. At least some of the electrical pins 402 are each individually coupled to a voltage generator (discussed more thoroughly below) within the controller 104. When connector 114 and wand connector 120 are coupled, each electrical pin 402 couples to a single electrical pin 302, and thus each illustrative electrical pin 402 couples to a single electrode 200 (FIG. 2). While FIG. 4 shows only four illustrative electrical pins, in some embodiments 26 or more electrical pins may be present in the wand connector 120.

Figure 5:
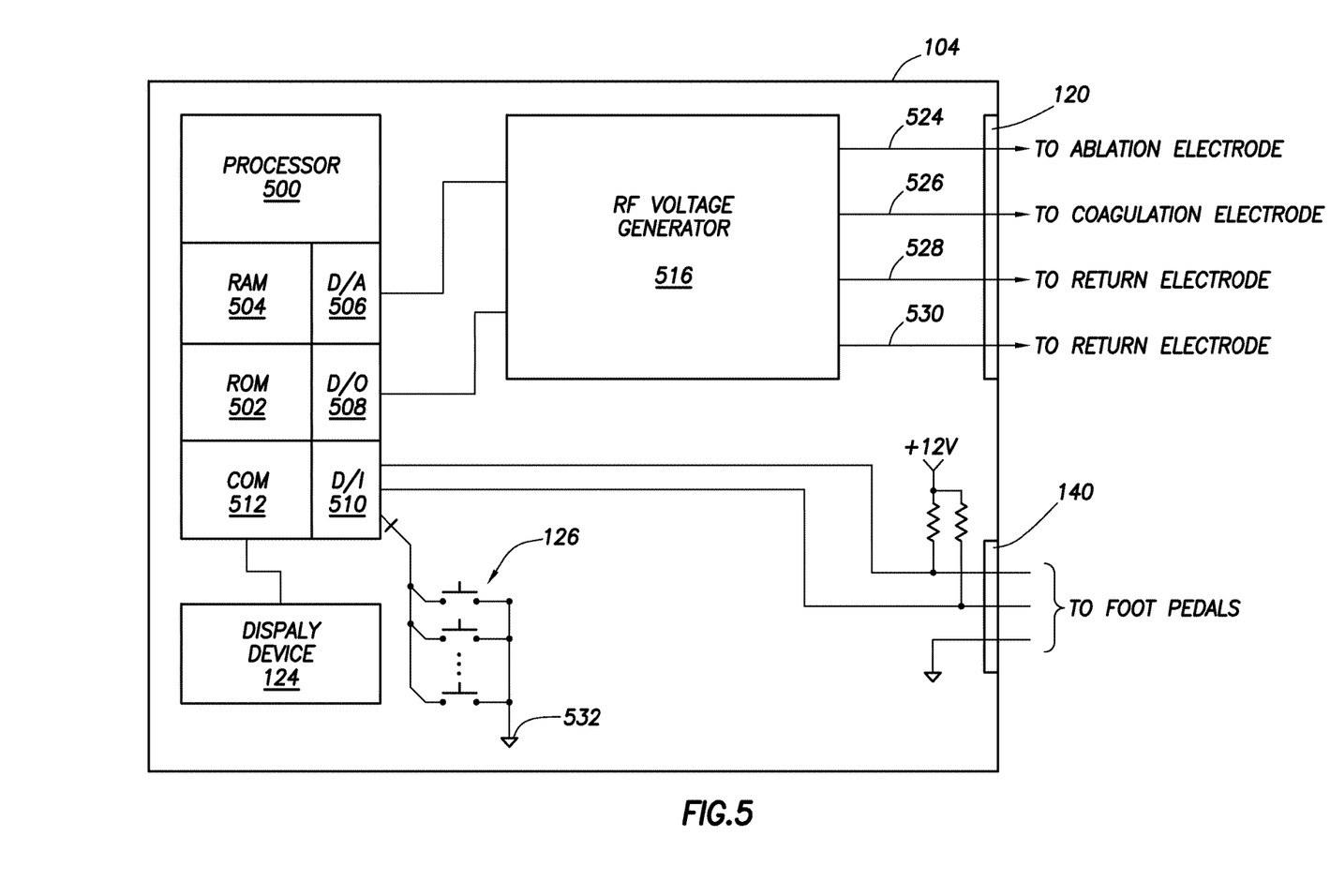
FIG. 5 shows an electrical block diagram of an electrosurgical controller in accordance with at least some embodiments.

FIG. 5 shows an electrical block diagram of controller 104 in accordance with at least some embodiments. In particular, the controller 104 comprises a processor 500. The processor 500 may be a microcontroller, and therefore the microcontroller may be integral with read-only memory (ROM) 502, random access memory (RAM) 504, digital-to-analog converter (D/A) 506, digital outputs (D/O) 508 and digital inputs (D/I) 510. The processor 500 may further provide one or more externally available peripheral busses, such as a serial bus (e.g., I$^2$C), parallel bus, or other bus and corresponding communication mode. The processor 500 may further be integral with a communication logic 512 to enable the processor 500 to communicate with external devices, as well as internal devices, such as display device 124. Although in some embodiments the controller 104 may be implemented in the form of a microcontroller, in yet other embodiments the processor 500 may be implemented as a standalone central processing unit in combination with individual RAM, ROM, communication, D/A, D/O and D/I devices, as well as communication port hardware for communication to peripheral components.

ROM 502 stores instructions executable by the processor 500. In particular, the ROM 502 may comprise a software program that implements the various embodiments of adjusting ablation and/or coagulation RF energy. The RAM 504 may be the working memory for the processor 500, where data may be temporarily stored and from which instructions may be executed. Processor 500 couples to other devices within the controller 104 by way of the digital-to-analog converter 506 (e.g., in some embodiment the RF generator 516), digital outputs 508 (e.g, in some embodiment the RF generator 516), digital inputs 510 (e.g., interface devices such as push button switches 126 foot pedal assembly 130 (FIG. 1)), communication device 512 (e.g., display device 124), and other peripheral devices.

Voltage generator 516 generates alternating current (AC) voltages that are applied to electrical pins in the wand connector 120 and ultimately to electrodes 200 of the wand 102. In some embodiments, the voltage generator 516 defines an ablation active terminal 524, coagulation active terminal 526, and one or more return terminals 528, 530. Each of the terminals 524, 526, 528 and 530 couple to electrical pins in the wand connector 120. The ablation active terminal 524 and coagulation active terminal 526 are the terminals upon which the voltages and electrical currents are induced by the voltage generator 516, and the return terminals 528, 530 provide a return path for electrical currents. It would be possible for the return terminals 528, 530 to provide a common or ground being the same as the common or ground within the balance of the controller 104 (e.g., the common 532 used on push-buttons 126), but in other embodiments the voltage generator 516 may be electrically "floated" from the balance of the controller 104, and thus the return terminals 528, 530, when measured with respect to the common or earth ground (e.g., common 532) may show a voltage; however, an electrically floated voltage generator 516 and thus the potential for voltage readings on the return terminals 528, 530 relative to earth ground does not negate the return terminal status of the terminals 528, 530 relative to the active terminals 524, 526.

The voltage generated and applied between an active terminal and return terminal by the voltage generator 516 is RF energy that, in some embodiments, has a frequency of between about 5 kilo-Hertz (kHz) and 20 Mega-Hertz (MHz), in some cases being between about 30 kHz and 2.5 MHz, in other cases being between about 50 kHz and 500 kHz, often less than 350 kHz, and often between about 100 kHz and 200 kHz. In some applications, a frequency of about 100 kHz is useful because target tissue impedance is much greater at 100 kHz. In other applications, such as procedures in or around the heart or head and neck, higher frequencies may be desirable (e.g., 400-600 kHz) to reduce low frequency current flow into the heart or the nerves of the head and neck.

The RMS (root mean square) voltage generated by the voltage generator 516 may be in the range from about 5 Volts (V) to 1800 V, in some cases in the range from about 10 V to 500 V, often between about 10 V to 400 V depending on the active electrode size, the operating frequency and the operation mode of the particular procedure or desired effect on the tissue (i.e., contraction, coagulation, cutting or ablation). The peak-to-peak voltage generated by the voltage generator 516 for ablation in some embodiments is a square waveform with a peak-to-peak voltage in the range of 10 V to 2000 V and in some cases in the range of 100 V to 1800 V and in other cases in the range of about 28 V to 1200 V, often in the range of about 100 V to 320V peak-to-peak (again, depending on the electrode size, number of electrodes the operating frequency and the operation mode). Lower peak-to-peak voltage is used for tissue coagulation, thermal heating of tissue, or collagen contraction and may be in the range from 50 V to 1500V, in some cases 100 V to 1000 V and in other cases 60 V to 130 V peak-to-peak (again, using a square waveform).

The voltage and current generated by the voltage generator 516 may be delivered in a series of voltage pulses or AC voltage with a sufficiently high frequency (e.g., on the order of 5 kHz to 20 MHz) such that the voltage is effectively applied continuously (as compared with, e.g., lasers claiming small depths of necrosis, which are pulsed about 10 Hz to 20 Hz). In addition, the duty cycle (i.e., cumulative time in any one-second interval that energy is applied) of the square wave voltage produced by the voltage generator 516 is on the order of about 50% for some embodiments as compared with pulsed lasers which may have a duty cycle of about 0.0001%. Although square waves are generated and provided in some embodiments, the various embodiments may be equivalently implemented with many applied voltage waveforms (e.g., sinusoidal, triangular).

The voltage generator 516 delivers average power levels ranging from several milliwatts to hundreds of watts per electrode, depending on the voltage applied to the target electrode for the target tissue being treated, and/or the maximum allowed temperature selected for the wand 102. The voltage generator 516 is configured to enable a user to select the voltage level according to the specific requirements of a particular neurosurgical procedure, cardiac surgery, arthroscopic surgery, dermatological procedure, ophthalmic procedures, open surgery, or endoscopic surgery procedure. For cardiac procedures and potentially for neurosurgery, the voltage generator 516 may have a filter that filters leakage voltages at frequencies below 100 kHz, particularly voltages around 60 kHz. Alternatively, a voltage generator 516 configured for higher operating frequencies (e.g., 300 kHz to 600 kHz) may be used in certain procedures in which stray low frequency currents may be problematic. A description of one suitable voltage generator 516 can be found in commonly assigned U.S. Pat. Nos. 6,142,992 and 6,235,020, the complete disclosure of both patents are incorporated herein by reference for all purposes.

In accordance with at least some embodiments, the voltage generated 516 is configured to limit or interrupt current flow when low resistivity material (e.g., blood, saline or electrically conductive gel) causes a lower impedance path between the return electrode(s) and the active electrode(s). Further still, in some embodiments the voltage generator 516 is configured by the user to be a constant current source (i.e., the output voltage changes as function of the impedance encountered at the wand 102).

In some embodiments, the various operational modes of the voltage generator 516 may be controlled by the processor 500 by way of digital-to-analog converter 506. For example, the processor 500 may control the output voltages by providing one or more variable voltages to the voltage generator 516, where the voltages provided by the digital-to-analog converter 506 are proportional to the voltages to be generated by the voltage generator 516. In other embodiments, the processor 500 may communicate with the voltage generator by way of one or more digital output signals from the digital output 508, or by way of packet based communications using the communication device 512 (the communication-based embodiments not specifically shown so as not to unduly complicate FIG. 5).

Figure 6:
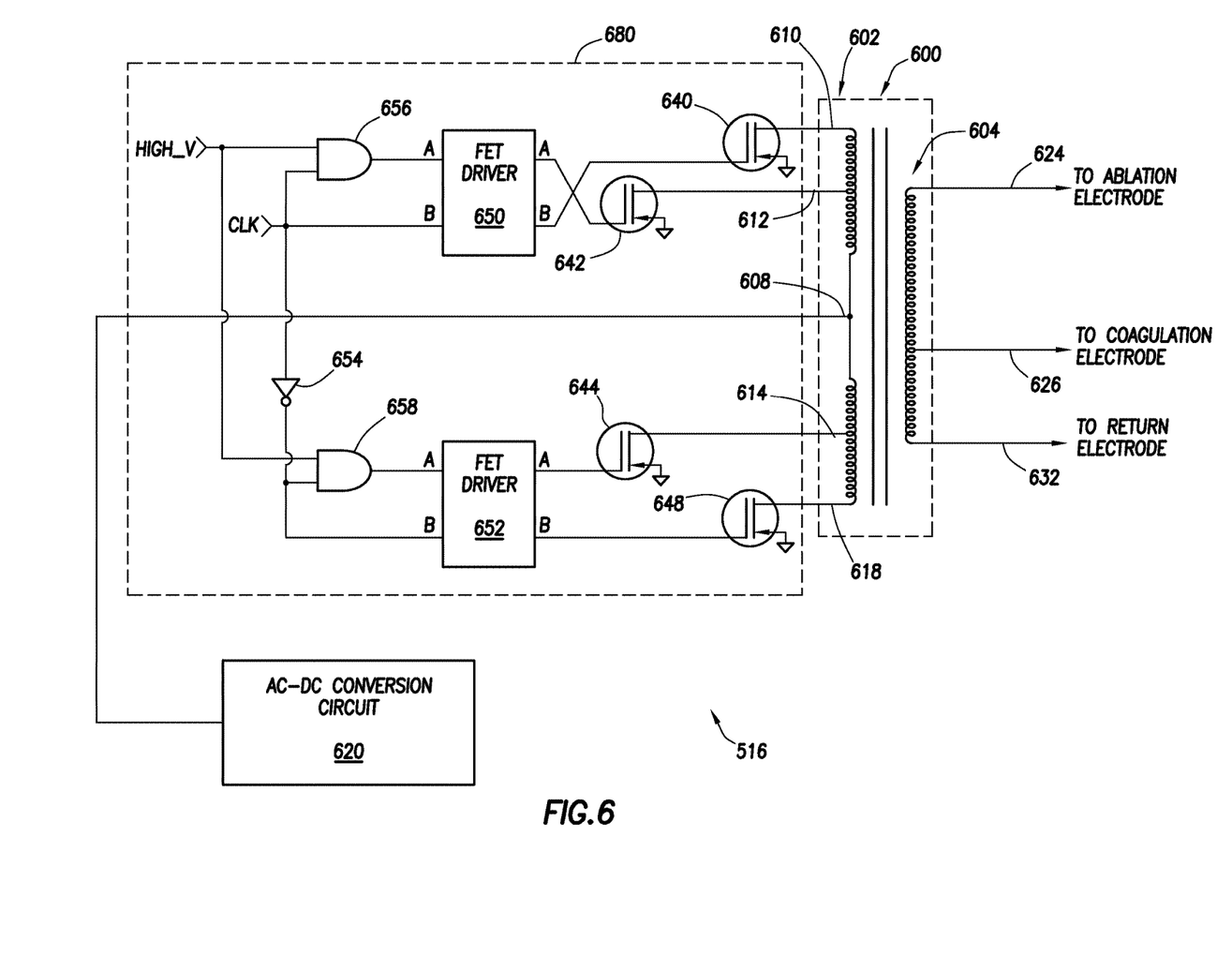
FIG. 6 shows an electrical block diagram of a voltage generator in accordance with at least some embodiments.

FIG. 6 shows at least some of the internal components of the voltage generator 516 in accordance with at least some embodiments. In particular, the voltage generator 516 comprises a transformer 600. The transformer 600 defines a primary winding 602 and a secondary winding 604. The secondary winding 604 has plurality of leads or terminals that couple to electrical pins of the wand connector 120 (FIG. 1). In the illustrative case of FIG. 6, the secondary winding 604 has ablation active terminal 624 (which may be the same as active terminal 524), coagulation active terminal 626 (which may be the same as terminal 526), and return terminal 632 (which may be the same as either terminal 528 or 530). The ablation active terminal 624 defines a particular number of turns of the secondary winding 604 relative to a return terminal (e.g., return terminal 632). Likewise, the coagulation active terminal 626 defines a particular number of turns of the secondary winding 604 relative to a return terminal (e.g., return terminal 632). Inasmuch as the ablation voltage is greater than a coagulation voltage, the number of turns defined by the ablation active terminal 624 is greater than the number of turns defined by the coagulation active terminal 626.

Still referring to FIG. 6, the primary winding 602 of the transformer 600 comprises a plurality of electrical taps (hereafter just taps). In the illustrative case of FIG. 6, the primary winding 602 comprises five total taps, including center tap 608, and taps 610, 612, 614, and 618. Each tap 610, 612, 614 and 618 defines a respective number of turns relative to the center tap 608. In some embodiments, the number of turns defined by taps 610 and 618 relative to the center tap 608 are approximately the same (i.e., within few turns), and the number of turns defined by taps 612 and 614 relative to the center tap 608 are approximately the same (i.e., within few turns), with the number of turns defined by taps 610 and 618 being greater than the number of turns defined by taps 612 and 614.

Each tap 610, 612, 614 and 618 is coupled to a control circuit 680. In particular, each tap 610, 612, 614 and 618 is coupled to an electrically controlled switch within the control circuit 680, the electrically controlled switch for each tap illustrated as field effect transistors (FETs) 640, 642, 644 and 648, respectively. Though FETs are illustrated, other electrically controlled switch devices (e.g., bipolar junction transistors, solid state relays, and electrically actuated mechanical relays) may be equivalently used. The center tap 608 is coupled to an alternating current (AC) to direct current (DC) (AC-to-DC) conversion circuit 620. The AC-to-DC conversion circuit 620 takes as input AC signals (e.g., 120 V AC signal from a wall socket), and creates a DC voltage or signal that couples to the center tap 608.

The voltage generator 516 in accordance with the various embodiments induces the RF energy on the secondary winding 604 by alternately forcing current from the DC signal at the center tap 608 through a portion of the primary winding 602 in a first direction, and then forcing current from the DC signal through a portion of the primary winding 602 in a second direction. Alternately forcing the current from the DC signal through the primary winding creates an AC signal applied to the primary winding 602, which AC signal induces voltages on the secondary windings 604.

Consider, as an explanation of using a DC signal coupled to the center tap 608 yet producing an AC primary winding signal, a positive DC signal applied at the center tap 608 and (for now) only FETs 642 and 644. Initially, for this example, FET 642 is made conductive drain-to-source and FET 644 is made non-conductive. Because the source of FET 642 is coupled to ground, a current flow is induced in the portion of the primary winding 602 between the center tap 608 and the tap 612. At a certain time thereafter, as a function of the desired frequency of the RF energy, FET 642 is made non-conductive and a short time later FET 644 is made conductive drain-to-source. The process repeats with current from the AC-to-DC conversion circuit 620 alternately flowing first one direction in the primary winding 602, and then the other direction, thus creating an AC signal in the primary winding 602 of the transformer 600.

The AC signal induced on the primary winding 602 by operation of the FETs 642 and 644 induces an AC voltage on the secondary winding 604, and thus AC voltages on the ablation active terminal 624 and coagulation active terminal 626. The magnitude of the voltage induced is a function of at least the magnitude of the DC voltage applied at the center tap 608 and the turns ratio of the transformer 600. As illustrated, the ablation active terminal 624 defines a greater number of turns than the coagulation active terminal 626, and thus the AC voltage on the ablation active terminal 624 will be greater than the AC voltage on the coagulation active terminal 626.

As illustrated in FIG. 6, however, the primary winding in accordance with at least some embodiments has more than two taps coupled to electrically controlled switches, and as illustrated the primary winding has four taps configured to couple to electrically controlled switches. Thus, illustrative control circuit 680 has four electrically controlled switches configured to couple to the primary winding 602. However, the primary winding 602 may have more taps (e.g., six, eight), and thus the control circuit 680 may have a corresponding number of electrically controlled switches. Multiple taps, and corresponding control switches, enables control of the number of turns of the primary winding 602 used in creation of secondary voltages.

In accordance with at least some embodiments, the ablation and coagulation voltages created by the voltage generator 516 are controlled, at least in part, by the number of turns of the primary winding 602 utilized. In the example above to explain creation of the AC signal by use of a DC signal coupled to the center tap 608, electrically controlled switches 642 and 644 were used, and electrically controlled switches 640 and 648 were assumed non-conductive drain-to-source. Thus, using only electrically controlled switches 642 and 644, particular output voltages were created.

Now consider a situation where a user of the controller 104 desires to change the ablation and coagulation voltage created. Such a change in voltage may be caused by using a different number of turns of the primary winding 602, and changing the number of turns may be implemented by using a different set of electrically controlled switches, such as electrically controlled switches 640 and 648. For the changed voltage setting in this example, the voltage of the DC signal applied to the center tap 608 is the same as in the previous example and is fixed. FETs 642 and 644 remain non-conductive drain-to-source, and the FETs 640 and 648 alternately are made conductive drain-to-source. When FET 640 is conductive and FET 648 is non-conductive, current from the DC signal flows from the center tap 608 to ground through FET 640. When FET 648 is conductive and FET 640 is non-conductive, current from the DC signal flows from the center tap 608 to ground through FET 648. The AC signal induced on the primary winding 602 by operation of the FETs 640 and 648 induces an AC voltage on the secondary winding 604, and thus AC voltages on the ablation active terminal 624 and coagulation active terminal 626. However, the number of turns used in this example with respect to use of FETS 640 and 648 are different than with respect to use of FETS 642 and 644, and thus the voltage induced on the secondary winding 604 is changed.

When illustrative FETs 642 and 644 are operational (and FETS 640 and 648 do not contribute), a first number of turns of the primary winding 602 are utilized (e.g., ten turns from the center tap to each of the taps 612 and 614). Given the number of turns of the secondary winding 604 (e.g., 350 turns from active electrode 624 to return electrode 632), a first turns ratio across the transformer is established. When FETs 640 and 648 are operational (and FETS 642 and 644 are not used), a second number of turns of the primary winding 602 are utilized (e.g., 30 turns from the center tap to each of the taps 610 and 618). Given the number of turns of the secondary winding 604, a second turns ratio across the transformer 600 is established, but the turns ratio in the second case is lower (given the higher number of primary turns) than the first turns ratio. It follows that higher voltages are induced on the secondary winding 604 with the first turns ratio, and a lower voltages are induced on the secondary winding 604 with the second turns ratio.

The control circuit 680 of FIG. 6 also comprises illustrative driving circuits for the FETs 640-648. In particular, FIG. 6 shows a FET driver 650 coupled to FETs 640 and 642, and FET driver 652 coupled to FETs 644 and 648. Each of the illustrative FET drivers 650 and 652 may be a part number TC4427 driver available from Microchip of Chandler, Ariz. Other integrated driver circuits, and driver circuits constructed from discrete components, may be equivalently used. The clock signal (CLK) provided to the driver circuits 650 and 652 may be generated within the voltage generator 516, or may be provided from an external source, such as the processor 500. The frequency and duty cycle of the clock signal may be selected based on the particular procedure that the controller 104 is used to perform. The illustrative signal to indicate a high voltage (HIGH_V) may be an asserted high signal provided to the voltage generator 516 from the processor 500 (e.g., based on user interaction with an interface device such as the buttons on the front panel of the controller 104, or the pedal system 130).

Consider first a situation where the HIGH_V signal is not asserted (here, a low voltage). Thus, the "A" input of each FET driver circuit 650 and 652 remains low because of the respective AND gates 656 and 658 block propagation of the clock signal given the low state of the HIGH_V signal. As the clock signal oscillates between a high voltage and a low voltage, the "B" input the FET driver circuit 650 follows the clock signal, and the gate of FET 640 is driven high with each high voltage state of the clock. The illustrative FETs 640-648 are N-Channel FETs, and are thus conductive drain-to-source when a high gate voltage is present. Thus, during periods of time when FET 640 has a high gate voltage, FET 640 is conductive drain-to-source. Likewise, the "B" input of the FET driver circuit 652 follows a logical NOT of the clock signal (because the clock signal applied to FET driver 652 first passes through NOT gate 654), and the gate of FET 648 is driven high with each low voltage state of the clock signal. In this case then, the current from the DC signal alternately flows from the center tap 608 through the FET 640 and FET 648, and a first voltage is induced on the terminals of the secondary winding 604.

Now consider the situation where the HIGH_V signal is asserted (here, a high voltage), indicating that a higher voltage is desired on the secondary winding 604. With the high voltage of the HIGH_V signal applied to each AND gate 656 and 658, the clock signal passes each respective AND gate and is applied to the "A" input of each FET driver circuit 650 and 652. Thus, as the clock signal oscillates between a high voltage and a low voltage, the "A" input of the FET driver circuit 650 follows the clock signal, and the gate of FET 642 is driven high with each high voltage state of the clock. Likewise, the "A" input of the FET driver circuit 652 follows a logical NOT of the clock signal (because the clock signal applied to FET driver circuit 652 first passes through NOT gate 654), and the gate of FET 644 is driven high with each low voltage state of the clock signal. Thus, current from the DC signal alternately flows from the center tap 608 through the FET 642 and FET 644. In this illustrative case, when FETs 642 and 644 are used, the primary winding 602 uses fewer turns, the turns ratio primary to secondary increases, and thus the voltages induced on the one or more secondary windings likewise increase.

In the specific implementation of FIG. 6, the clock signal is still applied to the "B" input of FET driver circuit 650, and the inverted clock signal is still applied to the "B" input of the FET driver circuit 652, even when the HIGH_V signal is asserted. Thus, when the HIGH_V signal is asserted FETs 640 and 642 each become conductive simultaneously, and FETs 644 and 648 each become conductive simultaneously; however, electrical current takes the path of least resistance, and thus the current flows to ground at the first opportunity, which is through FETs 642 and 644. Thus, the windings associated with FETs 640 and 648 do not carry electrical current in the situation when HIGH_V is asserted even though the FET are conductive drain-to-source. Other logical circuits to drive the FETs, including circuits which refrain from simultaneous activation, may be equivalently used.

In some embodiments, changes to the number the windings of the primary winding 602 utilized to create the voltages on the secondary winding 604 may take place infrequently. For example, the surgeon may change the output voltage (by changing the number of turns of the primary utilized), and use the output voltage for an extended period of time (e.g., minutes or hours). However, in other embodiments the changes to output voltage may take place every half cycle of the output voltage. Consider, as an example, a procedure where it is desirable that, for every half cycle of the output voltage, a voltage spike is provided. The voltage spike could be on the leading edge of the half cycle, or the trailing edge of the half cycle. For example, during a first portion of a half cycle, the HIGH_V signal could be asserted, and then de-asserted during the same half cycle. Thus, FET 642 would initially be conductive drain-to-source (while the HIGH_V signal is asserted), but would become non-conductive during the half cycle allowing current to flow through FET 640 (already conducting in the embodiments illustrated) during the remaining portion of the half cycle. Thus, initially a high voltage would be generated on the secondary winding 604, followed by a lower voltage, all within the same half cycle. Similar output voltage spikes could be generated by the FETs 644 and 648. In other embodiments, the voltage spike could be created near the end of the half cycle, rather than at the beginning.

The various embodiments discussed to this point have assumed a fixed voltage DC signal at the center tap 608. Thus, in spite of the fixed voltage DC signal at the center tap 608 on the primary winding 602, multiple output voltages on the secondary winding 604 can be created. Having a fixed voltage DC signal created by the AC-to-DC converter circuit 620 enables voltage generator 516 to have a relatively simple (and inexpensive) conversion circuit 620. In yet still further embodiments, the AC-to-DC conversion circuit 620 creates selectable voltage DC signals to apply to the center tap 608, and thus the voltage induced on the secondary winding 604 may be controlled not only by the number of turns of primary winding 602 utilized, but also the DC voltage applied to the center tap 608, thus enabling a broader range of control for the output voltages. The selectable DC voltage created by the AC-to-DC conversion circuit 620 could be created at the command of the processor 500 (such as commands sent by way of an analog signal from the D/A port 506, or one or more digital signals from the D/O port 508, or both) or by a circuit within control circuit 680 (not shown so as not to unduly complicate the figure).

Figure 7:
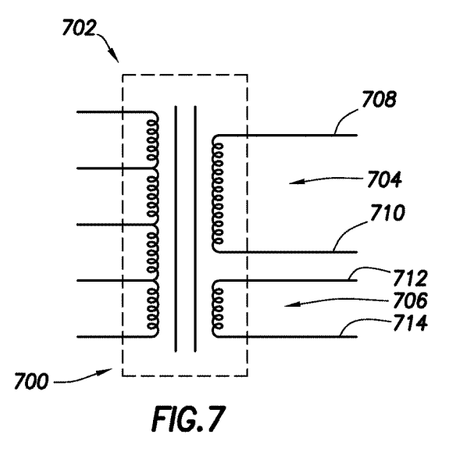
FIG. 7 shows a transformer in accordance with at least some embodiments.

The various embodiments of the voltage generator 516 discussed to this point have assumed that the ablation active electrode, coagulation active electrode and the return electrode are all derived from a shared secondary winding 604 and selective placements of leads. However, other variations are possible. For example, FIG. 7 shows embodiments of a transformer 700 for use in a voltage generator 516, the transformer 700 having a primary winding 702 (similar if not the same as primary winding 602). Additionally, in certain embodiments transformer 700 may have multiple secondary windings 704 and 706. Thus, illustrative transformer 700 may define an ablation active terminal 708 that defines a number of turns relative to an ablation return terminal 710. Voltages induced on ablation active terminal 708 of the secondary winding 704 are thus relative to the ablation return terminal 710. Likewise, illustrative transformer 700 may define a coagulation active terminal 712 that defines a number of turns relative to a coagulation return terminal 714. Voltages induced on coagulation active terminal 712 of the secondary winding 706 are thus relative to the coagulation return terminal 714.

Figure 8:
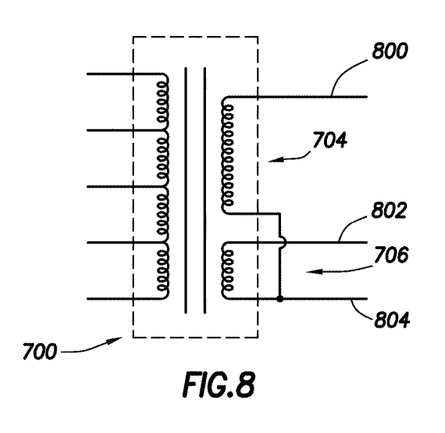
FIG. 8 shows a transformer in accordance with at least some embodiments.

FIG. 8 shows yet still further embodiments where transformer 700 is used, but the return terminals of the secondary windings 704 and 706 are electrically coupled. Thus, in voltage generators using a transformer 700 configured as in FIG. 8, the transformer 700 may define an ablation active terminal 800 that defines a number of turns relative to shared return terminal 804. Voltages induced on ablation active terminal 800 of the secondary winding 704 are thus relative to the shared return terminal 804. Likewise, illustrative transformer 700 configured as in FIG. 8 may define a coagulation active terminal 802 that defines a number of turns relative to shared return terminal 804. Voltages induced on coagulation active terminal 802 of the secondary winding 706 are thus relative to the shared return terminal 804.

Changes to the number of turns of the primary winding of the transformer affect both the ablation and coagulation voltages induced on the secondary winding(s), and the specification to this point has assumed that corresponding changes to the ablation and coagulation voltages are acceptable. However, there may be situations where a surgeon may need to change applied voltage for ablation (e.g., to provide a certain operational condition), yet no changes are needed in the coagulation voltage (e.g., the coagulation is close to optimal). Conversely, a surgeon may need to change applied voltage for coagulation (e.g., to provide better coagulation in the particular circumstance), yet no changes are needed in the ablation voltage (e.g., the ablation is close to optimal). To address the situation, and in accordance with other embodiments, the secondary winding may comprise multiple possible leads for an active terminal (ablation or coagulation), where each lead defines a different number of turns relative to a return lead, yet only one such lead couples to and thus becomes the active terminal.

Figure 9:
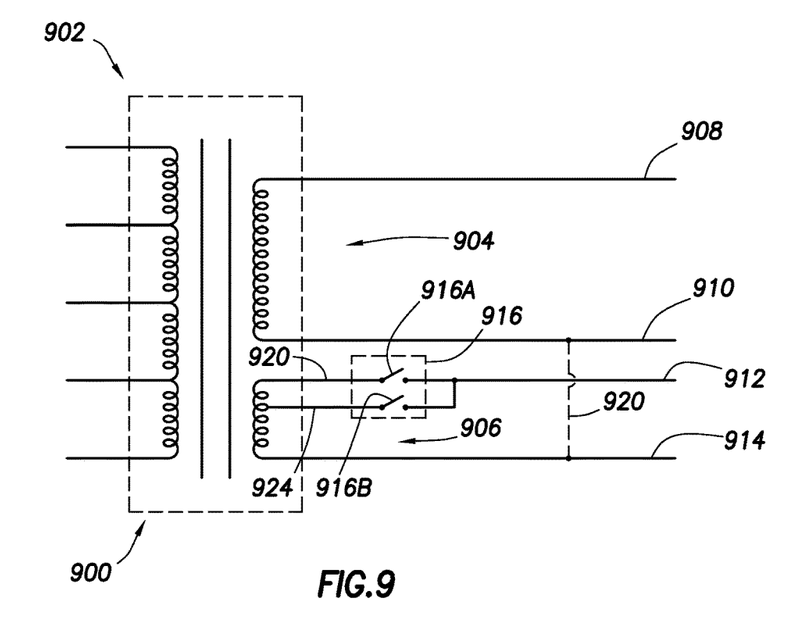
FIG. 9 shows a transformer with a relay circuit in accordance with at least some embodiments.

FIG. 9 illustrates embodiments where multiple active leads for one of the active terminals (in the case of FIG. 9, the coagulation active terminal) may be selected. In particular, the transformer 900 having a primary winding 902 (similar if not the same as primary windings 602 and 702), and multiple secondary windings 904 and 906. Secondary winding 904 may define an ablation active terminal 908 that defines a number of turns relative to an ablation return terminal 910. Voltages induced on ablation active terminal 908 of the secondary winding 904 are thus relative to the ablation return terminal 910. Likewise, illustrative secondary winding 906 may define a coagulation active terminal 912 that defines a number of turns relative to a coagulation return terminal 914. Voltages induced on coagulation active terminal 912 of the secondary winding 906 are thus relative to the coagulation return terminal 914. However, the secondary winding 906 has multiple leads that couple to a relay circuit 916. In particular, secondary winding 906 has two leads 920 and 924 that each couple to the relay circuit 916. The relay circuit 916 is configured to selectively, and mutually exclusively, couple either lead 920 or lead 924 to the coagulation active terminal 912 (which coagulation active terminal is then coupled to an electrical pin of the wand connector 120 (FIG. 1)).

Relay circuit 916 may be controlled by the control circuit 680 (which is controlled by the processor 500), or the relay circuit 916 may be coupled to and controlled directly by the processor 500. Further, while relay circuit 916 illustrates switches 916A and 916B as electrically actuated mechanical relays, in other embodiments the switches may be any electrically controlled device, such as FETs, bipolar junction transistors, or solid state relays.

Consider, as an example, a controller 104 having a voltage generator 516 that includes a transformer such as illustrated in FIG. 9. Further consider that the controller 104 is operated by a surgeon with switch 916A of the relay circuit 916 conducting and switch 916B not conducting. Further consider that the surgeon desires to increase the voltage on the ablation active electrode 908, but that a substantial change in the coagulation voltage is not desired. As discussed above, one or both of the number of turns of the primary winding 902 utilized or the DC signal applied to the center tap may be adjusted to effectuate the increased voltage on the ablation active terminal 908. However, with no modification to the state of the relay circuit 916, there will also be an increase in the voltage on the coagulation active terminal 912. In order to lower again the voltage on the coagulation active terminal 912, the controller 104 may change the state of the relay circuit 916 (open switch 916A, and close switch 916B) such that the turns ratio of the transformer with respect to the induced coagulation voltage is lowered. Thus, the surgeon's desire to increase an ablation voltage, and not proportionally increase the coagulation voltage, may be implemented in the embodiments illustrated in FIG. 9 by primary winding-side considerations as above, and operation of the relay circuit 916 to control the number of secondary winding turns used to create the coagulation voltage.

Before proceeding, there are a few additional points regarding FIG. 9 to consider. First, FIG. 9 shows a separate ablation return terminal and coagulation return terminal. However, the leads representing the returns can be coupled together (as shown by dashed line 920), and thus the ablation voltage and coagulation voltage may be relative to a shared return terminal. Next, while the relay circuit 916 is illustrated with respect to the coagulation voltage, in other embodiments the secondary winding that produces the ablation voltage may have multiple leads that couple to a relay circuit, and thus adjustments to the ablation voltage may be effectuated, in part, by selective coupling of particular leads (representing different turns ratios) to the ablation active terminal. Further still, both the first winding of the secondary winding that creates the ablation voltage and the second winding of the secondary winding that creates the coagulation voltage could have multiple leads and corresponding relay circuits. Finally, while FIG. 9 illustrates situations where separate secondary windings are used for creation of separate yet simultaneous ablation and coagulation outputs, in yet still further embodiments the multiple leads coupled to a relay circuit and on to an active terminal may originate from a single secondary winding, such as shown by transformer 600 (FIG. 6).

Figure 10:
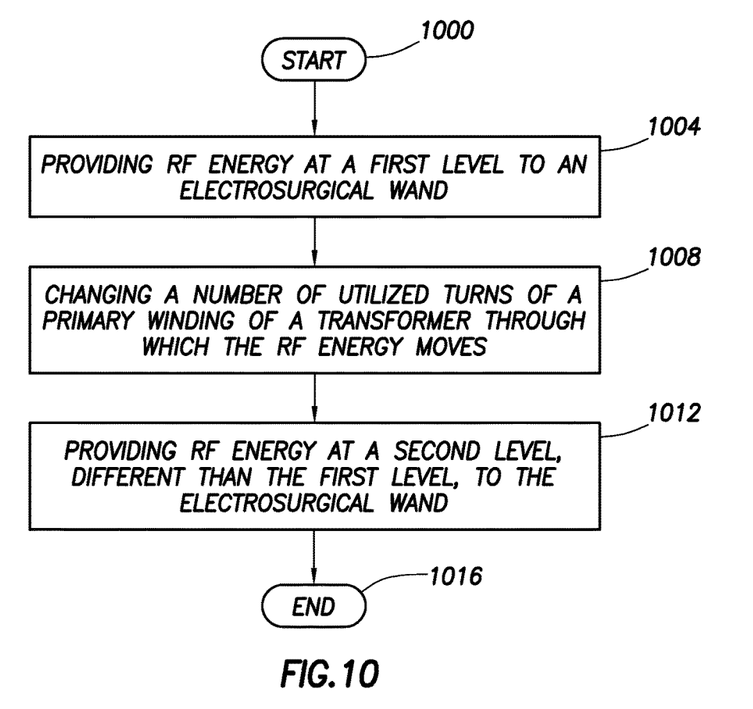
FIG. 10 shows a method in accordance with at least some embodiments.

FIG. 10 illustrates a method in accordance with at least some embodiments described herein. In particular, the method starts (block 1000) and proceeds to providing RF energy at a first level to an electrosurgical wand (block 1004). Then, the method moves to changing a number of utilized turns of a primary winding of a transformer through which the RF energy moves (block 1008). Next, RF energy is provided at a second level, different than the first level, to the electrosurgical wand (block 1012), and the method ends (block 1016). In some embodiments, a DC voltage applied to the primary winding remains unchanged when changing the number of turns utilized, but in other embodiments the DC voltage may likewise be selectively adjusted. In some cases the changing of the number of turns may take place within a half-cycle of the RF energy.

Figure 11:
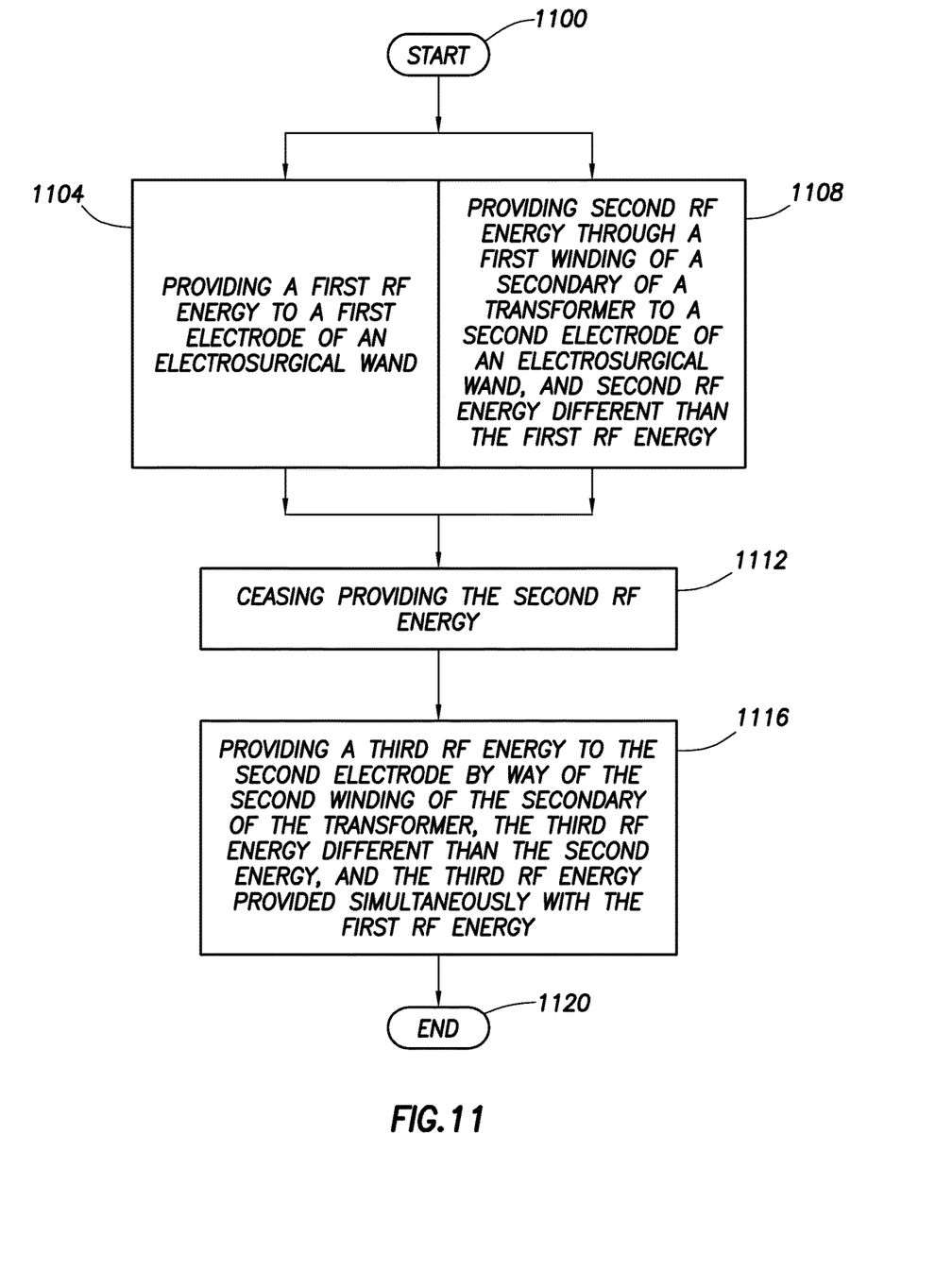
FIG. 11 shows a method in accordance with at least some embodiments.

FIG. 11 illustrates yet another method in accordance with the various embodiments described herein. In particular, the method starts (block 1100) and proceeds to providing a first RF energy to a first electrode of an electrosurgical wand (block 1104). Simultaneously with the providing the first RF energy (again block 1104), the method comprises providing second RF energy through a first winding of a secondary winding of a transformer to a second electrode of an electrosurgical wand (block 1108), and second RF energy different than the first RF energy. Next, the method involves ceasing providing the second RF energy (block 1112). And thereafter, providing a third RF energy to the second electrode by way of the second winding of the secondary winding of the transformer (block 1116), the third RF energy different than the second energy, and the third RF energy provided simultaneously with first RF energy. Thereafter, the method ends (block 1120). In some cases, the first winding and the second winding of the secondary winding of the transformer are independent windings, and in yet still other embodiments the first and second windings of the secondary winding are each a select number of a single windings of the secondary winding.

While preferred embodiments of this disclosure have been shown and described, modifications thereof can be made by one skilled in the art without departing from the scope or teaching herein. The embodiments described herein are exemplary only and are not limiting. For example, the FETs 640-648 of the control circuit 680 are illustrated as N-Channel FETs; however, P-Channel FETs, bipolar junction transistors and in some cases solid state relays may be equivalently used. Because many varying and different embodiments may be made within the scope of the present inventive concept, including equivalent structures, materials, or methods hereafter though of, and because many modifications may be made in the embodiments herein detailed in accordance with the descriptive requirements of the law, it is to be understood that the details herein are to be interpreted as illustrative and not in a limiting sense.

What is claimed is:

1. An electrosurgical controller comprising:
a wand connector disposed on an outer surface of the electrosurgical controller, the wand connector configured to couple to a connector of an electrosurgical wand, and the wand connector comprising a plurality of electrical pins; and
a voltage generator comprising:
a first active terminal coupled to a first electrical pin of the wand connector;
a first return terminal coupled to a second electrical pin of the wand connector; and
a transformer comprising a primary winding and a secondary winding, the secondary winding defines the first active and first return terminals;
the electrosurgical controller is configured to change a first output voltage on the first active terminal relative to the first return terminal by selective control of a number of turns of the primary winding used to create the output voltage.

2. The electrosurgical controller of claim 1 wherein the voltage generator further comprises:
an alternating current (AC) to direct current (DC) (AC-to-DC) conversion circuit configured to produce a DC output signal;
a center tap of the primary winding of the transformer, the center tap coupled to the DC output signal; and
a control circuit coupled to the primary winding, the control circuit configured to selectively control the number of turns of the primary winding used to create the first output voltage.

3. The electrosurgical controller of claim 2 wherein the voltage level of the DC output signal is fixed.

4. The electrosurgical controller of claim 2 wherein the AC-to-DC conversion circuit selectively changes a voltage level of DC output signal.

5. The electrosurgical controller of claim 2 wherein the voltage generator further comprises:
a first tap of the primary winding, the first tap defines a first number of turns relative to the center tap;

a second tap of the primary winding, the second tap defines a second number of turns relative to the center tap;

a third tap of the primary winding, the third tap defines a third number of turns relative to the center tap;

a fourth tap of the primary winding, the fourth tap defines a fourth number of turns relative to the center tap, the first and third taps define different number of turns than the second and fourth taps;

a first through fourth electrically controlled switches coupled one each to the first through fourth taps, respectively, each electrically controlled switch configured to selectively couple its respective tap to ground; and the voltage generator configured to selectively control the number of turns of the primary winding used to create the first output voltage by selective activation of the electrically controlled switches.

6. The electrosurgical controller of claim 5 wherein each electrically controlled switch is a field effect transistor (FET).

7. The electrosurgical controller of claim 1 further comprising an interface device, the interface device configured to accept commands from a user of the electrosurgical controller, and the electrosurgical controller configured to change the first output voltage based on user interaction with the interface device.

8. The electrosurgical controller of claim 1 further comprising:

a second active terminal of the secondary winding, the second active terminal coupled a third electrical pin of the wand connector, the first active terminal relative to the first return terminal defines a first number of turns, the second active terminal relative to the first return terminal defines a second number of turns, and the first number of turns different than the second number of turns; and the electrosurgical controller is configured to change a second output voltage on the second active terminal relative to the first return terminal by selective control of a number of turns of the primary winding utilized.

9. The electrosurgical controller of claim 8, wherein the voltage generator is configured so that the first output voltage is sufficient to create an ionized vapor layer on an ablation electrode disposed at a distal end of the electrosurgical wand, and so that the second output voltage is sufficient to coagulate tissue adjacent to a first coagulation electrode disposed at the distal end of the electrosurgical wand.

10. The electrosurgical controller of claim 1 further comprising:

a second active terminal of the secondary winding, the second active terminal coupled a third electrical pin of the wand connector; and a second return terminal of the secondary winding, the second return terminal coupled to fourth electrical pin of the wand connector, the first active terminal relative to the first return terminal defines a first number of turns, the second active terminal relative to the second return terminal defines a second number of turns, and the first number of turns different than the second number of turns; and the electrosurgical controller is configured to change a second output voltage on the second active terminal relative to the second return terminal by selective control of a number of turns of the primary winding utilized.

11. The electrosurgical controller of claim 10, wherein the first active terminal is electrically coupled to a first ablation electrode disposed at a distal end of the electrosurgical wand and the second active terminal is electrically coupled to a first coagulation electrode disposed at the distal end of the electrosurgical wand.

12. The electrosurgical controller of claim 10, wherein the first output voltage is sufficient to ablate tissue, and wherein the second output voltage is insufficient to ablate tissue and sufficient to coagulate blood at the tissue.

13. The electrosurgical controller of claim 1 further comprising:

the first active terminal relative to the first return terminal defines a first number of turns;

a second active terminal of the secondary winding, the second active terminal relative to the first return terminal defines a second number of turns;

a third active terminal of the secondary winding, the third active terminal relative to the first return terminal defines a third number of turns, the first number of turns different than both second and third number of turns, and the second number of turns different than the third number of turns;

a relay circuit coupled to the second and third active terminals, the relay circuit configured to selectively, and mutually exclusively, couple the second and third active leads to a third electrical pin of the wand connector.

14. The electrosurgical controller of claim 1 further comprising:

the first active terminal relative to the first return terminal defines a first number of turns;

a second return terminal of the secondary winding, the second return terminal coupled to a third electrical pin of the wand connector;

a second active terminal of the secondary winding, the second active terminal defines a second number of turns relative to the second return terminal;

a third active terminal of the secondary winding, the third active terminal defines a third number of turns relative to the second return terminal, the first number of turns different than both second and third number of turns, and the second number of turns different that the third number of turns; and a relay circuit coupled to the second and third active terminals, the relay circuit configured to selectively, and mutually exclusively, couple the second and third active terminals to a fourth electrical pin of the wand connector.

* * * * *